(12) United States Patent
Qu et al.

(10) Patent No.: US 9,561,376 B2
(45) Date of Patent: Feb. 7, 2017

(54) SYSTEMS AND METHODS FOR ESTIMATING INTRACARDIAC DISTANCE USING SENSED ELECTRICAL PULSES

(71) Applicant: Pacesetter, Inc., Sunnyvale, CA (US)

(72) Inventors: Fujian Qu, San Jose, CA (US); Hoda Razavi, San Jose, CA (US); Yelena Nabutovsky, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 66 days.

(21) Appl. No.: 14/609,196

(22) Filed: Jan. 29, 2015

(65) Prior Publication Data

US 2016/0220819 A1    Aug. 4, 2016

(51) Int. Cl.
*A61N 1/36* (2006.01)
*A61N 1/368* (2006.01)
*A61N 1/365* (2006.01)
*A61N 1/362* (2006.01)

(52) U.S. Cl.
CPC ........... *A61N 1/3686* (2013.01); *A61N 1/3627* (2013.01); *A61N 1/36578* (2013.01)

(58) Field of Classification Search
CPC . A61N 1/3686; A61N 1/3627; A61N 1/36578
See application file for complete search history.

(56) References Cited

U.S. PATENT DOCUMENTS 7,657,313 B2 *   2/2010   Rom .................. A61N 1/36514
                                                                  607/17
2007/0191901 A1   8/2007  Schecter
2011/0230746 A1   9/2011  Jarverud et al.

* cited by examiner

*Primary Examiner* — Joseph Dietrich
(74) *Attorney, Agent, or Firm* — Theresa A. Raymer

(57) ABSTRACT

The present disclosure provides systems and methods for estimating a change in an intracardiac distance between systole and diastole. A system includes a pacing electrode configured to generate a pacing pulse, a sensing electrode configured to measure an electrical artifact corresponding to the pacing pulse, and a computing device communicatively coupled to the pacing electrode and the sensing electrode, the computing device configured to determine a first amplitude of a first electrical artifact measured at the sensing electrode during systole, determine a second amplitude of a second electrical artifact measured at the sensing electrode during diastole, and calculate a mechanical index based on the first amplitude and the second amplitude, wherein the mechanical index is representative of the change in the intracardiac distance.

20 Claims, 5 Drawing Sheets

SYSTEMS AND METHODS FOR ESTIMATING INTRACARDIAC DISTANCE USING SENSED ELECTRICAL PULSES

FIELD OF THE DISCLOSURE

The present disclosure relates generally to cardiac stimulation systems, and more particularly to estimating changes in intracardiac distances between systole and diastole to facilitate cardiac resynchronization therapy optimization and device programming.

BACKGROUND ART

Heart failure (HF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all HF patients suffer debilitating symptoms immediately. Some may live actively for years. Yet, with few exceptions, the disease is relentlessly progressive. As HF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Current standard treatment for HF is typically centered around medical treatment using ACE inhibitors, diuretics, and digitalis. It has also been demonstrated that aerobic exercise may improve exercise tolerance, improve quality of life, and decrease symptoms. Cardiac surgery has also been performed on a small percentage of patients with particular etiologies. Although advances in pharmacological therapy have significantly improved the survival rate and quality of life of patients, some HF patients are refractory to drug therapy, have a poor prognosis and limited exercise tolerance. In recent years cardiac pacing, in particular Cardiac Resynchronization Therapy (CRT), has emerged as an effective treatment for many patients with drug-refractory HF.

Long-term clinical benefits of CRT are influenced by patient selection, lead placement, and device programming. For example, a variety of intracardiac electrogram (IEGM) based algorithms have been developed to predict which atrioventricular (AV) and interventricular conduction (VV) delays will facilitate maximizing clinical benefits. For a viable myocardium, mechanical contraction is coupled with electrical conduction. Given that restoration of both mechanical and electrical synchrony is important for CRT optimization, it would be desirable to have a mechanically-based evaluation technique that facilitates comparisons between different CRT settings.

BRIEF SUMMARY OF THE DISCLOSURE

In one embodiment, the present disclosure is directed to a system for estimating a change in an intracardiac distance between systole and diastole. The system includes a pacing electrode configured to generate a pacing pulse, a sensing electrode configured to measure an electrical artifact corresponding to the pacing pulse, and a computing device communicatively coupled to the pacing electrode and the sensing electrode, the computing device configured to determine a first amplitude of a first electrical artifact measured at the sensing electrode during systole, the first electrical artifact corresponding to a first pacing pulse generated by the pacing electrode, determine a second amplitude of a second electrical artifact measured at the sensing electrode during diastole, the second electrical artifact corresponding to a second pacing pulse generated by the pacing electrode, and calculate a mechanical index based on the first amplitude and the second amplitude, wherein the mechanical index is representative of the change in the intracardiac distance.

In another embodiment, the present disclosure is directed to a computing device for estimating a change in an intracardiac distance between systole and diastole, the computing device configured to be communicatively coupled to a pacing electrode configured to generate a pacing pulse and a sensing electrode configured to measure an electrical artifact corresponding to the pacing pulse. The computing device includes a memory, and a processing device communicatively coupled to the memory, the processing device configured to determine a first amplitude of a first electrical artifact measured at the sensing electrode during systole, the first electrical artifact corresponding to a first pacing pulse generated by the pacing electrode, determine a second amplitude of a second electrical artifact measured at the sensing electrode during diastole, the second electrical artifact corresponding to a second pacing pulse generated by the pacing electrode, and calculate a mechanical index based on the first amplitude and the second amplitude, wherein the mechanical index is representative of the change in the intracardiac distance.

In another embodiment, the present disclosure is directed to a method for estimating a change in an intracardiac distance between systole and diastole. The method includes generating during systole, at a pacing electrode, a first pacing pulse, measuring, at a sensing electrode, a first electrical artifact that corresponds to the first pacing pulse, generating during diastole, at the pacing electrode, a second pacing pulse, measuring, at the sensing electrode, a second electrical artifact that corresponds to the second pacing pulse, determining a first amplitude of the first electrical artifact, determining a second amplitude of the second electrical artifact, and calculating a mechanical index based on the first amplitude and the second amplitude, wherein the mechanical index is representative of the change in the intracardiac distance.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for estimating a change in an intracardiac distance between systole and diastole. A system includes a pacing electrode configured to generate a pacing pulse, a sensing electrode configured to measure an electrical artifact corresponding to the pacing pulse, and a computing device communicatively coupled to the pacing electrode and the sensing electrode, the computing device configured to determine a first amplitude of a first electrical artifact measured at the sensing electrode during systole, determine a second amplitude of a second electrical artifact measured at the sensing electrode during diastole, and calculate a mechanical index based on the first amplitude and the second amplitude, wherein the mechanical index is representative of the change in the intracardiac distance.

Figure 1A:
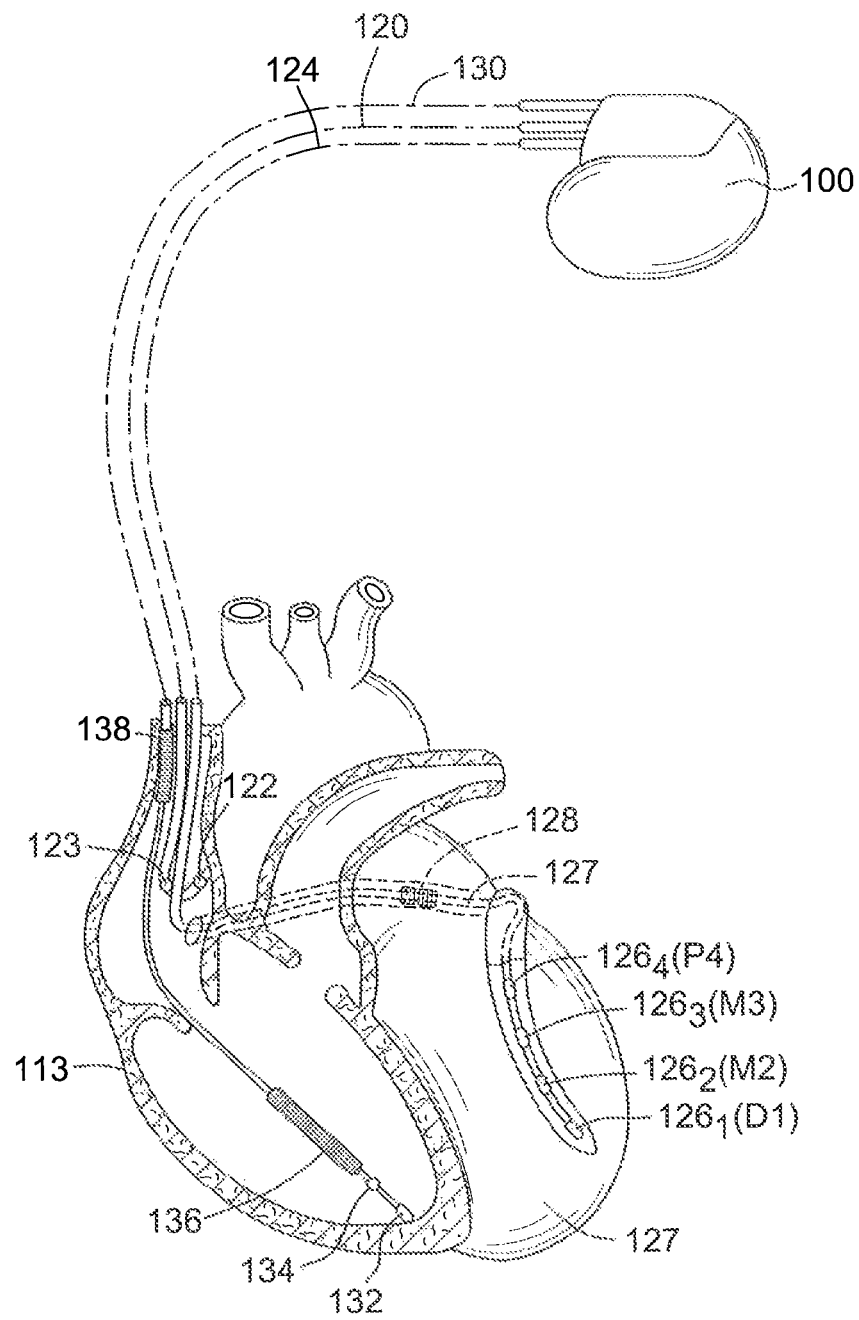
FIG. 1A is a simplified, partly cutaway view illustrating an implantable stimulation device in electrical communication with at least three leads implanted into a patient's heart for delivering multi-chamber stimulation and shock therapy and sensing cardiac activity.

With reference to FIGS. 1A and 1, a description of an example pacemaker/implantable cardioverter-defibrillator (ICD) 100 will now be provided. FIG. 1A is a simplified block diagram of pacemaker/ICD 100, which is a dual-chamber stimulation device capable of treating both fast and slow arrhythmias with stimulation therapy, including cardioversion, defibrillation, and pacing stimulation, including multi-site left ventricular (MSLV) pacing. To provide atrial chamber pacing stimulation and sensing, pacemaker/ICD 100 is shown in electrical communication with a heart 113 by way of a right atrial (RA) lead 120 having an atrial tip electrode 122 and an atrial ring electrode 123 implanted in the atrial appendage. Pacemaker/ICD 100 is also in electrical communication with heart 113 by way of a right ventricular (RV) lead 130 having, in this embodiment, a ventricular tip electrode 132, a RV ring electrode 134, a RV coil electrode 136, and a superior vena cava (SVC) coil electrode 138. Typically, RV lead 130 is transvenously inserted into the heart so as to place RV coil electrode 136 in the RV apex, and SVC coil electrode 138 in the superior vena cava. Accordingly, RV lead 130 is capable of receiving cardiac signals, and delivering stimulation in the form of pacing and shock therapy to the right ventricle (also referred to as the RV chamber).

To sense left atrial and ventricular cardiac signals and to provide left chamber pacing therapy, pacemaker/ICD 100 is coupled to a multi-pole left ventricular (LV) lead 124 designed for placement in the "CS region" for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the coronary sinus (CS), great cardiac vein, left marginal vein, left posterior ventricular vein, middle cardiac vein, small cardiac vein, and/or any other cardiac vein accessible by the CS. Accordingly, an example LV lead 124 is designed to receive atrial and ventricular cardiac signals and to deliver left ventricular pacing therapy using a set of four LV electrodes $126_1$, $126_2$, $126_3$, and $126_4$ (thereby providing a quadra-pole lead), left atrial pacing therapy using at least a LA ring electrode 127, and shocking therapy using at least a LA coil electrode 128. In some embodiments, LV lead 124 includes LV electrodes $126_1$, $126_2$, $126_3$, and $126_4$, but does not include LA ring and coil electrodes 127 and 128. Such a lead can be, e.g., the Quartet™ left ventricular pacing lead developed by St. Jude Medical Inc. (headquartered in St. Paul, Minn.), which includes four pacing electrodes on the left ventricular lead— enabling up to ten pacing configurations LV electrode $126_1$ is shown as being the most "distal" LV electrode (with relation to how far the electrode is from where LV lead 124 connects to pacemaker/ICD 100). For example LV electrode $126_1$ may be located at the apex of the left ventricle. LV electrode $126_4$ is shown as being the most "proximal" LV electrode. For example LV electrode $126_4$ may be located at the base of the left ventricle. LV electrodes $126_2$ and $126_3$ are shown as being "middle" LV electrodes, between distal and proximal LV electrodes $126_1$ and $126_4$. Accordingly, the four LV electrodes $126_1$, $126_2$, $126_3$, and $126_4$ can be referred to respectively as electrodes D1, M2, M3 and P4 (where "D" stands for "distal", "M" stands for "middle", and "P" stands from "proximal", and the numbers are arranged from most distal to most proximal). It is also possible that more or fewer LV electrodes are provided. However, for much of the remaining discussion, it will be assumed that the multi-pole LV lead 124 includes four LV electrodes $126_1$, $126_2$, $126_3$, and $126_4$ (i.e., LV electrodes D1, M2, M3 and P4, respectively).

LV electrodes $126_1$, $126_2$, $126_3$, and $126_4$ can be used to provide various pacing vectors and sensing vectors. Some of the vectors are intraventricular LV vectors (vectors between two LV electrodes); whereas others are interventricular vectors (e.g., vectors between an LV electrode and RV coil 136). Below is a list of exemplary vectors that can be used for pacing and/or sensing using LV electrodes D1, M2, M3 and P4 with and without the RV coil 136. In the following list, the first electrode in each row (i.e., the electrode to the left of the arrow) is assumed to be connected as the cathode, and the second electrode in each row (i.e., the electrode to the right of the arrow) is assumed to be connected as the anode, but that need not be the case, especially where neither electrode is a coil.

D1→RV coil
M2→RV coil
M3→RV coil
P4→RV coil
D1→M2
D1→P4
M2→P4
M3→M2
M3→P4
P4→M2

Alternative and/or additional vectors, other than those listed above, can be used for pacing and/or sensing. Although only three leads are shown in FIG. 1A, it should also be understood that additional leads (with one or more pacing, sensing and/or shocking electrodes) might be used and/or additional electrodes might be provided on the leads already shown, such as additional electrodes on the RV or LV lead. It is also possible that less than three leads be used.

Figure 1B:
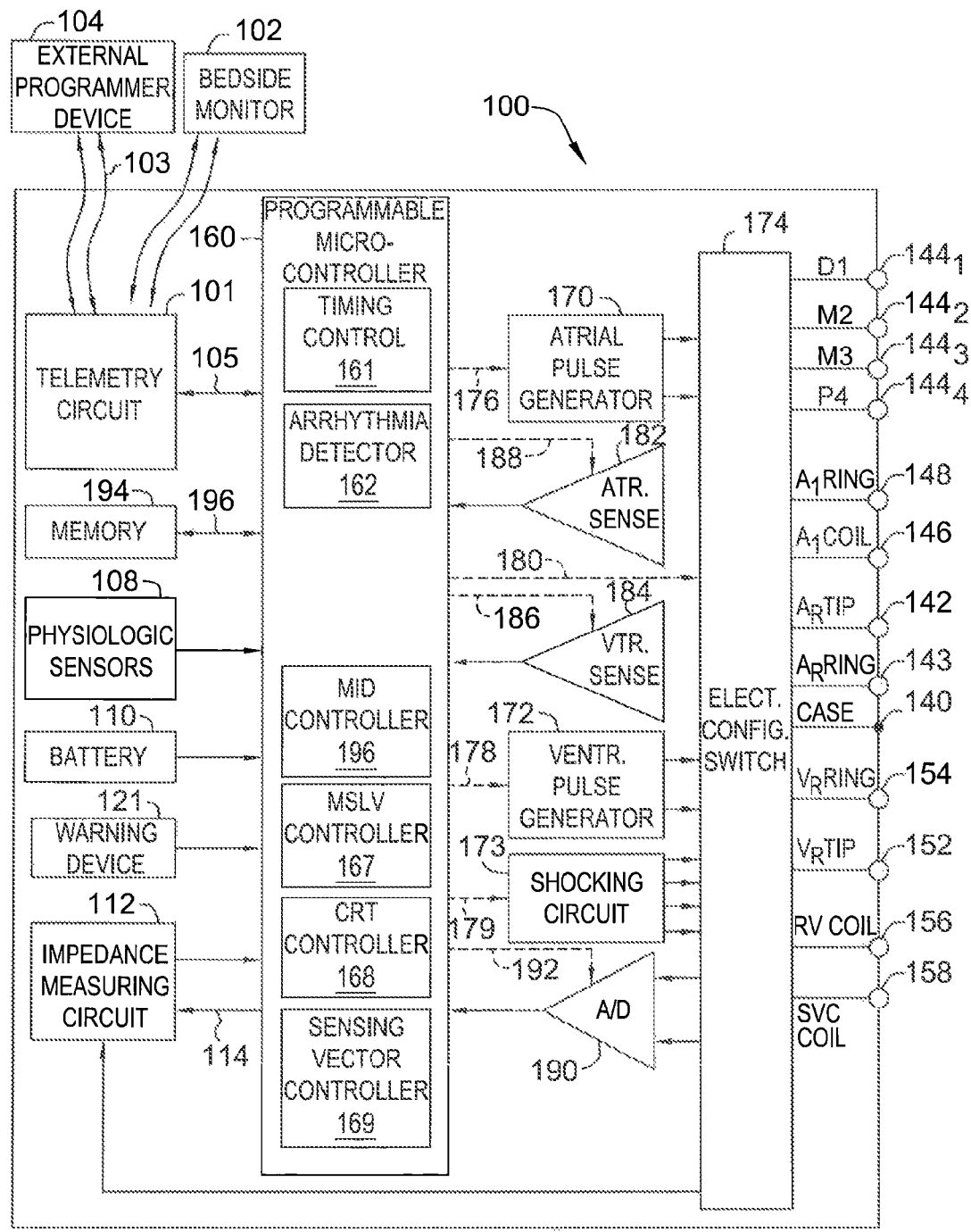
FIG. 1B is a functional block diagram of the multi-chamber implantable stimulation device of FIG. 1A, illustrating the basic elements that provide pacing stimulation, cardioversion, and defibrillation in four chambers of the heart.

A simplified block diagram of internal components of pacemaker/ICD 100 is shown in FIG. 1B. While a particular pacemaker/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. A housing 140 for pacemaker/ICD 100, shown schematically in FIG. 1B, is often referred to as the "can", "case" or "case electrode" and may be programmably selected to act as the return electrode for all "unipolar" modes. Housing 140 may further be used as a return electrode alone or in combination with one or more of coil electrodes, 128, 136 and 138 for shocking purposes. Housing 140 further includes a connector (not shown) having a plurality of terminals, 142, 143, $144_1$-$144_4$, 146, 148, 152, 154, 156 and 158 (shown schematically and, for convenience, the names of the electrodes to which they are connected are shown next to the terminals). As such, to achieve RA sensing and pacing, the connector includes at least an RA tip terminal ($A_R$ TIP) 142 adapted for connection to the atrial tip electrode 122 and an RA ring ($A_R$ RING) electrode 143 adapted for connection to RA ring electrode 123. To achieve left chamber sensing, pacing and shocking, the connector includes an LV tip terminal $144_1$ adapted for connection to the D1 electrode and additional LV electrode terminals $144_2$, $144_3$ and $144_4$ terminals adapted for connection to the M2, M3 and P4 electrodes of quadra-pole LV lead 124.

The connector also includes an LA ring terminal ($A_L$ RING) 146 and an LA shocking terminal ($A_L$ COIL) 148, which are adapted for connection to LA ring electrode 127 and the LA coil ($A_L$ COIL) electrode 128, respectively. To support right chamber sensing, pacing and shocking, the connector further includes an RV tip terminal ($V_R$ TIP) 152, an RV ring terminal ($V_R$ RING) 154, an RV shocking terminal ($V_R$ COIL) 156, and an SVC shocking terminal (SVC COIL) 158, which are adapted for connection to RV tip electrode 132, RV ring electrode 134, RV coil electrode 136, and SVC coil electrode 138, respectively.

At the core of pacemaker/ICD 100 is a programmable microcontroller 160, which controls the various modes of stimulation therapy. As is well known in the art, microcontroller 160 (also referred to herein as a control unit or controller) typically includes a microprocessor, or equivalent control circuitry, designed specifically for controlling the delivery of stimulation therapy and may further include RAM or ROM memory, logic and timing circuitry, state machine circuitry, and I/O circuitry. Typically, microcontroller 160 includes the ability to process or monitor input signals (data) as controlled by a program code stored in a designated block of memory.

As shown in FIG. 1B, an atrial pulse generator 170 and a ventricular pulse generator 172 generate pacing stimulation pulses for delivery by RA lead 120, RV lead 130, and/or LV lead 124 via an electrode configuration switch 174. Microcontroller 160 includes timing control circuitry 161 to control the timing of the stimulation pulses, including, but not limited to, pacing rate, atrio-ventricular (AV) delay, interatrial conduction (AA) delay, interventricular conduction (W) delay and/or intraventricular delay (e.g., LV1-LV2 delay). Timing control circuitry 161 can also keep track of timing of refractory periods, blanking intervals, noise detection windows, evoked response detection windows, alert intervals, marker channel timing, etc.

Microcontroller 160 further includes an arrhythmia detector 162 that can be utilized by the stimulation device 100 for determining desirable times to administer various therapies. Additional components of the microcontroller include a MSLV controller 167 to control the actual delivery of MSLV pacing and a cardiac resynchronization therapy (CRT) controller 168 to control CRT, which can be performed in conjunction with MSLV pacing.

Microcontroller 160 is also shown as including a sensing vector controller 169 that can be used, e.g., to control the electrode configuration switch 174 (e.g., via control signals 180) to selectively connect specific electrode(s) to sensing circuits 182 or 184 as a cathode or an anode, to achieve the various sensing vectors that are used to obtain IEGMs in accordance with embodiments described herein. Where multiple sensing vectors are being used to obtain a plurality of IEGMs indicative of cardiac electrical activity at a plurality of ventricular regions, sensing circuit 184 may include multiple channels (e.g., duplicate circuitry) to enable sensing of more than one ventricular IEGM signal at the same time, and/or sensing circuit 184 may use time divisional multiplexing to sense more than one ventricular IEGM signal.

Depending upon the implementation, the various components of the microcontroller may be implemented as separate software modules or the modules may be combined to permit a single module to perform multiple functions. For example, the MSLV controller and the CRT controller 168 can be combined. In addition, although shown as being components of the microcontroller, some or all of these components may be implemented separately from the microcontroller, using application specific integrated circuits (ASICs) or the like.

Switch 174 includes a plurality of switches for connecting the desired electrodes to the appropriate I/O circuits, thereby providing complete electrode programmability. Accordingly, switch 174, in response to a control signal 180 from microcontroller 160, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 182 and ventricular sensing circuits 184 may also be selectively coupled to RA lead 120, LV lead 124, and RV lead 130, through switch 174 for detecting the presence of cardiac activity in each of the four chambers of the heart. Accordingly, the atrial (ATR. SENSE) and ventricular (VTR. SENSE) sensing circuits, 182 and 184, may include dedicated sense amplifiers, multiplexed amplifiers or shared amplifiers. Switch 174 determines the "sensing polarity" of the cardiac signal by selectively closing the appropriate switches, as is also known in the art. In this way, a clinician may program the sensing polarity independent of the stimulation polarity. Each sensing circuit, 182 and 184, preferably employs one or more low power, precision amplifiers with programmable gain and/or automatic gain control, bandpass filtering, and a threshold detection circuit, as known in the art, to selectively sense the cardiac signal of interest. The automatic gain control enables pacemaker/ICD 100 to deal effectively with the difficult problem of sensing the low amplitude signal characteristics of atrial or ventricular fibrillation. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are applied to the inputs of an analog-to-digital (A/D) data acquisition system 190. Data acquisition system 190 is configured to acquire intracardiac electrogram signals, convert the raw analog data into a digital signal, and store the digital signals for later processing and/or telemetric transmission to an external programmer 104 or a bedside monitor or personal advisory module (PAM) 102. Data acquisition system 190 is coupled to RA lead 120, LV lead 124, and RV lead 130 through switch 174 to sample cardiac signals across any pair of desired electrodes. Microcontroller 160 is further coupled to a memory 194 by a suitable data/address bus 196, wherein the programmable operating parameters used by microcontroller 160 are stored and modified, as required, in order to customize the operation of pacemaker/ICD 100 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each pacing and shocking pulse to be delivered to the patient's heart within each respective tier of therapy. Other pacing parameters include base rate, rest rate and circadian base rate.

Advantageously, the operating parameters of implantable pacemaker/ICD 100 may be non-invasively programmed into memory 194 through a telemetry circuit 101 in telemetric communication with external device 104 or bedside monitor 102, such as a programmer, transtelephonic transceiver, or a diagnostic system analyzer. The telemetry circuit 101 is activated by the microcontroller by a control signal 106. Telemetry circuit 101 advantageously allows intracardiac electrograms and status information relating to the operation of pacemaker/ICD 100 (as contained in microcontroller 160 or memory 194) to be sent to external device 104 and/or bedside monitor 102 through an established communication link 103. An internal warning device 121 (also referred to as a patient alert) may be provided for generating perceptible warning signals to the patient via vibration, voltage or other methods.

Pacemaker/ICD 100 further includes an accelerometer or other physiologic sensor 108, commonly referred to as a "rate-responsive" sensor because it is typically used to adjust pacing stimulation rate according to the exercise state of the patient. Pacemaker/ICD additionally includes a battery 110 that provides operating power to the circuits shown in FIG. 1B. As further shown in FIG. 1B, pacemaker/ICD 100 is shown as having an impedance measuring circuit 112, which is enabled by the microcontroller 160 via a control signal 114. Uses for an impedance measuring circuit include, but are not limited to, lead impedance surveillance during the acute and chronic phases for proper lead positioning or dislodgement; detecting operable electrodes and automatically switching to an operable pair if dislodgement occurs: measuring respiration or minute ventilation; measuring thoracic impedance for determining shock thresholds; detecting when the device has been implanted; measuring respiration; and detecting the opening of heart valves, etc. Impedance measuring circuit 112 is advantageously coupled to switch 174 so that any desired electrode may be used.

In the case where pacemaker/ICD 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, microcontroller 160 further controls a shocking circuit 173 by way of a control signal 179. Shocking circuit 173 generates shocking pulses of low (up to 0.1 joules), moderate (0.1-10 joules) or high energy (11 to 40 joules or more), as controlled by the microcontroller 160. Such shocking pulses are applied to the heart of the patient through at least two shocking electrodes, and as shown in this embodiment, selected from LA coil electrode 128, RV coil electrode 136, and/or SVC coil electrode 138. Housing 140 may act as an active electrode in combination with RV electrode 136, or as part of a split electrical vector using SVC coil electrode 138 or LA coil electrode 128 (i.e., using RV electrode 136 as a common electrode).

In this embodiment, microcontroller 160 further includes a mechanical index (MID) controller 196. MID controller 196 calculates one or more MID values, as described in more detail below.

Pacemaker/ICD 100 is provided as an example. One or ordinary skill in the art would understand that embodiments described herein can be used with alternative types of implantable devices. Accordingly, embodiments described herein should not be limited to use only with the above described device.

As described below, Pacemaker/ICD 100 Pacemaker/ICD 100 may be used estimate intracardiac distances by measuring changes in amplitudes of sensed electrical pulses. MIDs representative of the estimated distances may be used to facilitate optimizing CRT settings.

More specifically, a pacing electrode (e.g., one of LV electrodes $126_1$, $126_2$, $126_3$, and $126_4$) delivers a stimulation, or pacing pulse, and a sensing electrode (e.g., a different one of LV electrodes $126_1$, $126_2$, $126_3$, and $126_4$) senses an electrical artifact corresponding to the stimulation pulse. The difference, or change, in amplitude between the stimulation pulse and the sensed electrical artifact is indicative of the physical distance between the pacing electrode and the sensing electrode. Accordingly, a first pacing pulse can be delivered at end-diastole to estimate the distance between the pacing electrode and the sensing electrode at diastole, and a second pacing pulse can be delivered at the absolute refractory period of the systolic phase to estimate the distance between the pacing electrode and the sensing electrode at systole.

The change in amplitude of the sensed electrical artifact between diastole and systole may be used to calculate a mechanical index (MID), as described herein. The MID reflects a relative change in ventricular dimension from diastole to systole. The MID can be measured for different CRT settings (e.g., combinations of atrioventricular pacing delay (AVD), interventricular conduction delays (VVD), multipoint pacing (MPP), etc.). The setting with the largest relative change in ventricular dimension (corresponding to stroke volume and ejection fraction) is generally the most desirable, or optimum, setting.

Figure 2:
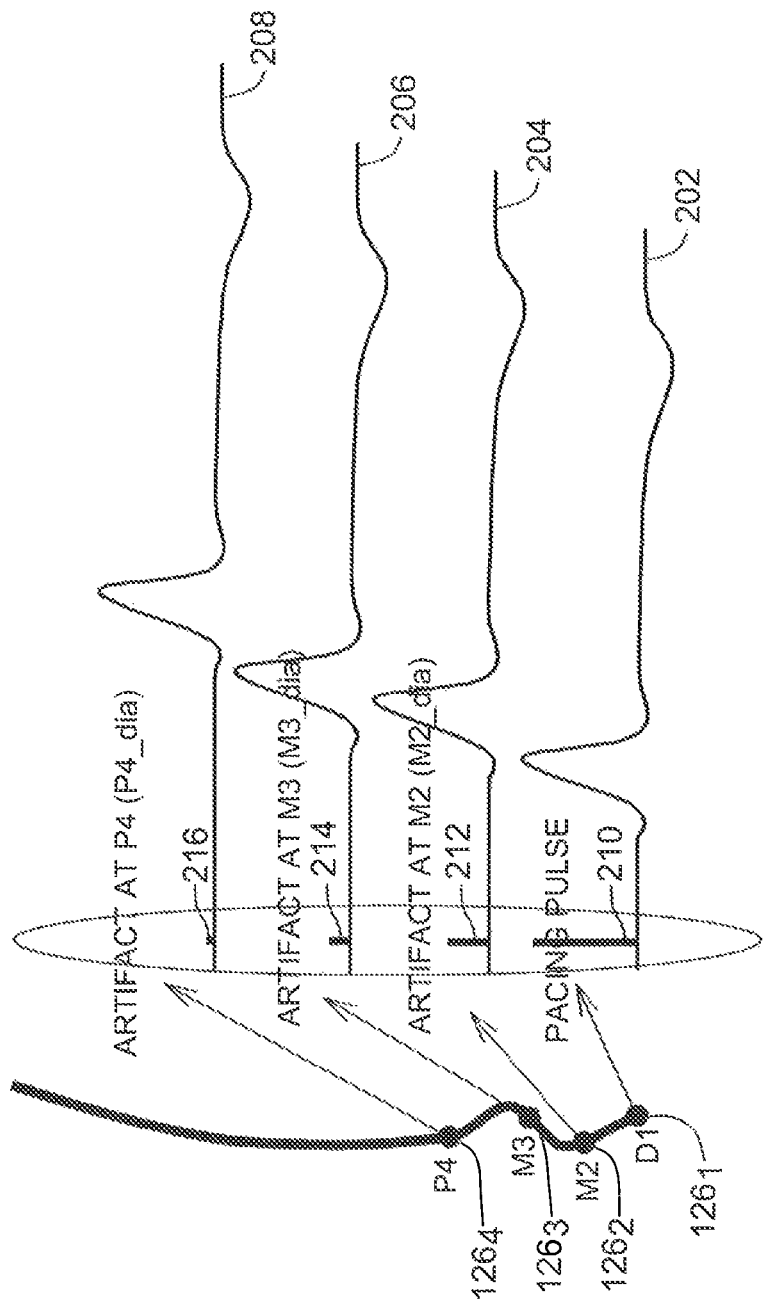
FIG. 2 is a schematic diagram illustrating determining a change in amplitude between a pacing pulse and a sensed electrical artifact at diastole.

FIG. 2 is a schematic diagram illustrating determining a change in amplitude between a pacing pulse and a sensed electrical artifact at diastole. FIG. 2 shows a first voltage trace 202 for LV electrode $126_1$ (i.e., distal electrode), a second voltage trace 204 for LV electrode $126_2$ (i.e., first middle electrode), a third voltage trace 206 for LV electrode $126_3$ (i.e., second middle electrode), and a fourth voltage trace 208 for LV electrode $126_4$ (i.e., proximal electrode). Voltages traces 202, 204, 206, and 208 are measured, for example, by recording an intracardiac electrogram (IEGM) for each electrode. The recorded IEGMs may be stored, for example, on memory 194 (shown in FIG. 1B).

In the embodiment of FIG. 2, distal electrode $126_1$ functions as the pacing electrode. That is, distal electrode $126_1$ generates a pacing pulse 210. Alternatively, any electrode, including electrodes separate from LV lead 124 (e.g., atrial tip electrode 122, atrial ring electrode 123, ventricular tip electrode 132, RV ring electrode 134, RV coil electrode 136, and superior vena cava (SVC) coil electrode 138) may deliver pacing pulse 210. Further, any suitable electrode may function as a sensing electrode.

In this embodiment, pacing electrode $126_1$ emits a single pulse. Alternatively, in some embodiments, pacing electrode $126_1$ may generate a plurality of consecutive pacing pulses having different amplitudes, which may facilitate easier detection of changes in amplitude. Moreover, the duration of the pacing pulse, the amplitude of the pacing pulse, and/or the sample rate at which IEGMs are recorded may be varied in different embodiments.

As shown in FIG. 2, each of first middle electrode $126_2$, second middle electrode $126_3$, and proximal electrode $126_4$ senses an associated electrical artifact 212, 214, 216 as a consequence of pacing pulse 210. Notably, the further the electrode from distal electrode $126_1$, the smaller the magnitude of the electrical artifact. That is, the magnitude of electrical artifact 212 is less than the magnitude of pacing pulse 210, the magnitude of electrical artifact 214 is less than the magnitude of electrical artifact 212, and the magnitude of electrical artifact 216 is less than the magnitude of electrical artifact 214. Accordingly, the magnitudes of electrical artifacts 212, 214, 216 are proportional to the distance between distal electrode $126_1$ and sensing electrodes $126_2$, $126_3$, and $126_4$.

Figure 3:
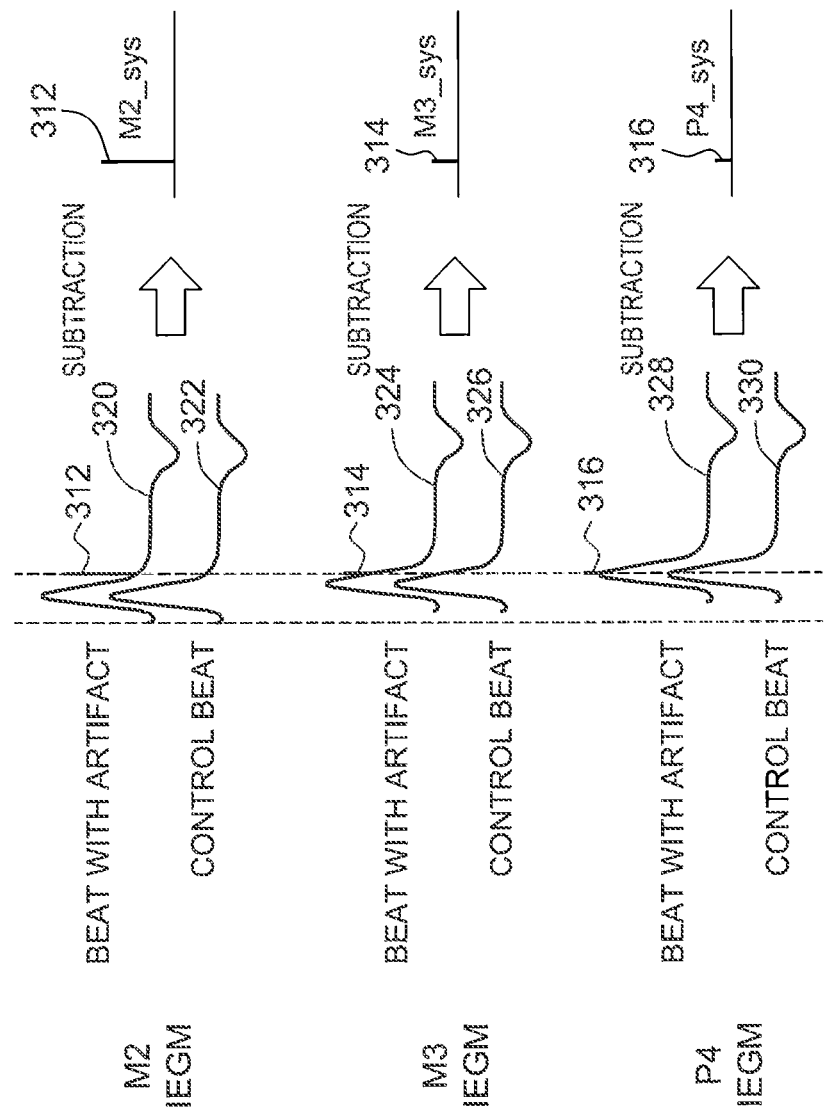
FIG. 3 is a schematic diagram illustrating determining a change in amplitude between a pacing pulse and a sensed electrical artifact at systole.

FIG. 3 is a schematic diagram illustrating determining a change in amplitude between a pacing pulse and a sensed electrical artifact at systole. In contrast to diastole, at systole, the heart generates electrical activity. Accordingly, at systole, determining the change in amplitude between the pacing pulse (not shown in FIG. 3), and electrical artifacts 312, 314, 316 is less straightforward.

FIG. 3 shows a first artifact voltage trace 320 and a first control voltage trace 322 for first middle electrode $126_2$, a second artifact voltage trace 324 and a second control voltage trace 326 for second middle electrode $126_3$, and a third artifact voltage trace 328 and a third control voltage trace 330 for proximal electrode $126_4$. Artifact voltage traces 320, 324, and 328 are the voltage traces acquired by electrodes $126_2$, $126_3$, and $126_4$ when a pacing pulse is delivered. In contrast, control voltage traces 322, 326, and 330 are the voltage traces sensed by electrodes $126_2$, $126_3$, and $126_4$ in the absence of a pacing pulse. Voltages traces 320, 322, 324, 326, 328, and 330 are measured, for example, by recording an intracardiac electrogram (IEGM) for each electrode. The recorded IEGMs may be stored, for example, on memory 194 (shown in FIG. 1B).

Accordingly, in this embodiment, to isolate the electrical artifact, a control voltage trace is subtracted from an associated artifact voltage trace. This subtraction may be performed, for example, by MID controller 196 (shown in FIG. 1A). That is, first control voltage trace 322 may be subtracted from first artifact voltage trace 320 to isolate electrical artifact 312, second control voltage trace 326 may be subtracted from second artifact voltage trace 324 to isolate electrical artifact 314, and third control voltage trace 330 may be subtracted from second artifact voltage trace 328 to isolate electrical artifact 316.

Figure 4:
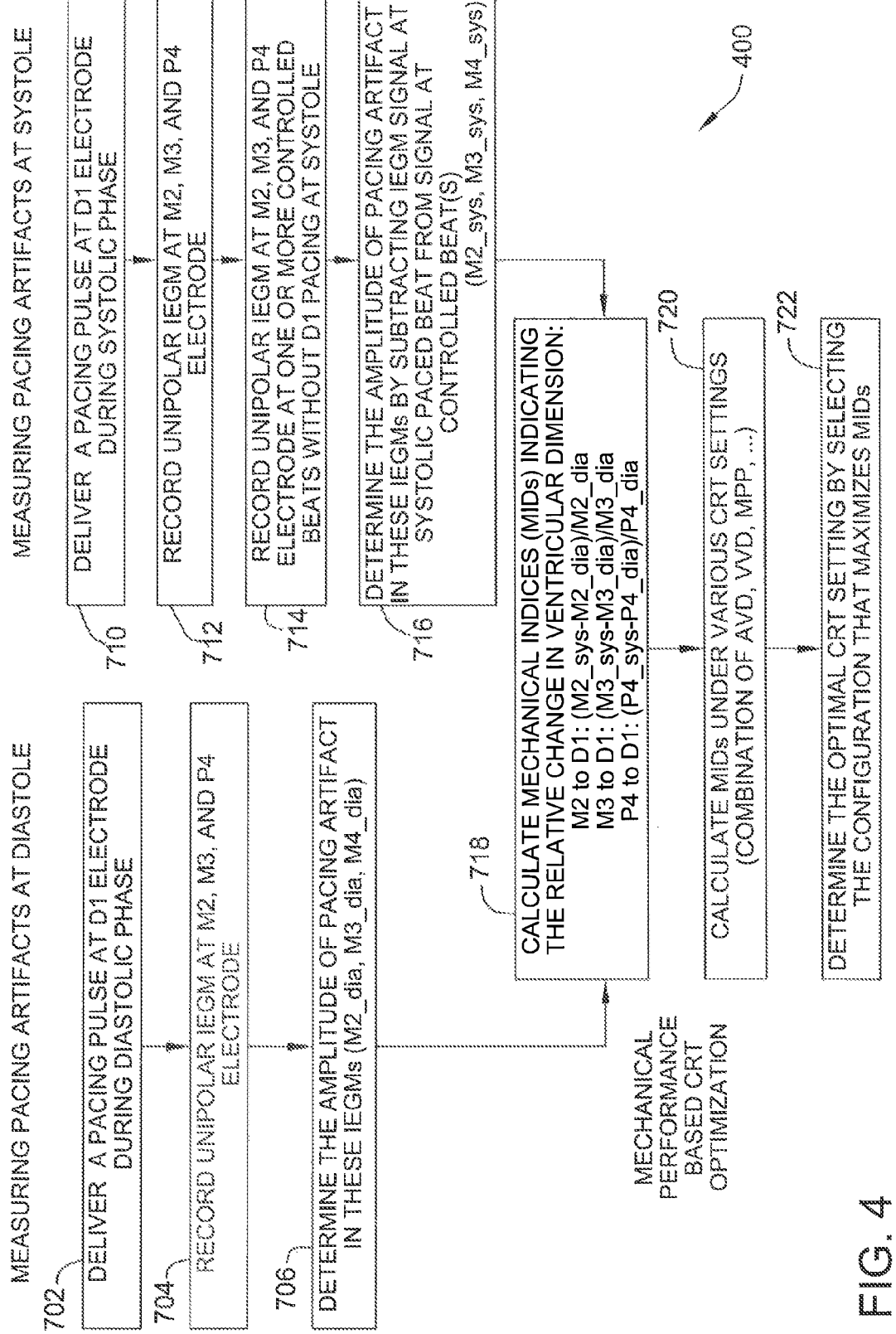
FIG. 4 is a flowchart of an example method for calculating mechanical indices (MIDs)

As noted above, the change in amplitude between the pacing pulse and the electrical artifact is used to calculated one or more MIDs. FIG. 4 is a flowchart illustrating an example method 400 of calculating MIDs. Although FIG. 4 describes calculating MIDs in accordance with the techniques described with reference to FIGS. 2 and 3, those of skill in the art will appreciate that method 400 may be modified to calculate any suitable MID.

For measuring pacing artifacts at diastole (i.e., as in FIG. 2), at block 702, a pacing pulse is delivered by distal electrode $126_1$ during a diastolic phase. At block 704, unipolar IEGMs are recorded for each of sensing electrodes $126_2$, $126_3$, and $126_4$. At block 706, the amplitude of the electrical, or pacing, artifacts in each recorded IEGM is determined.

For measuring pacing artifacts at systole (i.e., as in FIG. 3), at block 710, a pacing pulse is delivered by distal electrode $126_1$ during a systolic phase. At block 712, artifact unipolar IEGMs including electrical artifacts are recorded for each of sensing electrodes $126_2$, $126_3$, and $126_4$. At block 714, control unipolar IEGMs (i.e., not including electrical artifacts) are recorded for each of sensing electrodes $126_2$, $126_3$, and $126_4$. At block 716, the amplitude of the electrical, or pacing, artifacts for each sensing electrode $126_2$, $126_3$, and $126_4$ is determined by subtracting each recorded control IEGM from an associated artifact IEGM.

At block 718, MIDs indicating the relative change in ventricular distance between diastole and systole are calculated from the results in blocks 706 and 716. In this embodiment, a MID between sensing electrode $126_2$ and distal electrode $126_1$ is calculated by subtracting the amplitude of the electrical artifact at sensing electrode $126_2$ at diastole from the amplitude of the electrical artifact at sensing electrode $126_2$ at systole, and dividing that result by the amplitude of the electrical artifact at sensing electrode $126_2$ at diastole. MIDs between sensing electrodes $126_3$ and $126_4$ and distal electrode $126_1$ are similarly calculated. Alternatively, MIDs may be calculated using any suitable formula.

As indicated by block 720, the MIDs are calculated for a plurality of CRT settings (e.g., combinations of atrioventricular pacing delay (AVD), interventricular conduction delays (VVD), multipoint pacing (MPP), etc.). At block 722, the MIDs for different CRT settings are compared to determine an optimal CRT setting (i.e., the CRT corresponding to the largest MID). For example, if the MID between sensing electrode $126_2$ and distal electrode $126_1$ at a first CRT setting is greater than the MID between sensing electrode $126_2$ and distal electrode $126_1$ at a second CRT setting, the first setting is an improvement over the second setting. The MIDs for different CRT settings may be compared by a user (e.g., a physician), or may be automatically compared by microcontroller 160. In embodiments where microcontroller 160 performs the comparison, microcontroller 160 may report the results of the comparison to a user via external programmer 104 and/or bedside monitor 102.

In some embodiments, other parameters may be calculated based on the MIDs, and those parameters are compared to determine the optimal CRT setting. For example, in one embodiment, for each CRT setting of interest, an average of the MIDs between each of sensing electrodes $126_2$, $126_3$, and $126_4$ and distal electrode $126_1$ is calculated as a parameter. Those of skill in the art will appreciate that there are a number of other suitable parameters that can be calculated and compared.

For example, in another embodiment, for three electrodes (e.g., electrode A, B, and C), a first MID is calculated between electrode A and B, a second MID is calculated between electrode B and C, and a third MID is calculated between electrode A and C. A sum of the first, second, and third MIDs is then representative of a change (between systole and diastole) in area of a triangle defined by electrodes A, B, and C. Accordingly, this sum may be a parameter used to facilitate optimizing CRT settings.

The systems and methods described herein facilitate estimating intracardiac distances. By calculating MIDs representative of changes in intracardiac distances between diastole and systole, and comparing MIDs calculated for different CRT settings, the methods and systems described herein facilitate optimizing CRT settings for a subject, as described herein.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for estimating a change in an intracardiac distance between systole and diastole, the system comprising:
   a pacing electrode configured to generate a pacing pulse;
   a sensing electrode configured to measure an electrical artifact corresponding to the pacing pulse; and
   a computing device communicatively coupled to the pacing electrode and the sensing electrode, the computing device configured to:
      determine a first amplitude of a first electrical artifact measured at the sensing electrode during systole, the first electrical artifact corresponding to a first pacing pulse generated by the pacing electrode;
      determine a second amplitude of a second electrical artifact measured at the sensing electrode during diastole, the second electrical artifact corresponding to a second pacing pulse generated by the pacing electrode; and
      calculate a mechanical index based on the first amplitude and the second amplitude, wherein the mechanical index is representative of the change in the intracardiac distance.

2. The system of claim 1, further comprising a multiple-electrode lead that comprises the pacing electrode and the sensing electrode.

3. The system of claim 1, wherein the pacing electrode and the sensing electrode are both left ventricular electrodes.

4. The system of claim 1, wherein to determine the first amplitude, the computing device is configured to subtract a control intracardiac electrogram (IEGM) that does not include the first electrical artifact from an artifact IEGM that does include the first electrical artifact.

5. The system of claim 1, wherein to calculate the mechanical index, the computing device is configured to calculate the mechanical index as the difference between the first amplitude and the second amplitude, divided by the second amplitude.

6. The system of claim 1, wherein the computing device is configured to calculate a separate said mechanical index at each of a plurality of different cardiac resynchronization therapy (CRT) settings.

7. The system of claim 6, wherein the computing device is configured to:
   compare the calculated mechanical indices to determine which calculated mechanical index is the largest; and
   select the CRT settings determined to have the largest mechanical index for use during further CRT pacing.

8. A computing device for estimating a change in an intracardiac distance between systole and diastole, the computing device configured to be communicatively coupled to a pacing electrode configured to generate a pacing pulse and a sensing electrode configured to measure an electrical artifact corresponding to the pacing pulse, the computing device comprising:
   a memory; and
   a processing device communicatively coupled to the memory, the processing device configured to:
      determine a first amplitude of a first electrical artifact measured at the sensing electrode during systole, the first electrical artifact corresponding to a first pacing pulse generated by the pacing electrode;
      determine a second amplitude of a second electrical artifact measured at the sensing electrode during diastole, the second electrical artifact corresponding to a second pacing pulse generated by the pacing electrode; and
      calculate a mechanical index based on the first amplitude and the second amplitude, wherein the mechanical index is representative of the change in the intracardiac distance.

9. The computing device of claim 8, wherein the computing device is configured to be communicatively coupled to a multiple-electrode lead that includes the pacing electrode and the sensing electrode.

10. The computing device of claim 8, wherein the computing device is configured to be communicatively coupled to left ventricular electrodes that include the pacing electrode and the sensing electrode.

11. The computing device of claim 8, wherein to determine the first amplitude, the processing device is configured to subtract a control intracardiac electrogram (IEGM) that does not include the first electrical artifact from an artifact IEGM that does include the first electrical artifact.

12. The computing device of claim 8, wherein to calculate the mechanical index, the processing device is configured to calculate the mechanical index as the difference between the first amplitude and the second amplitude, divided by the second amplitude.

13. The computing device of claim 8, wherein the processing device is configured to calculate a separate said mechanical index at each of a plurality of different cardiac resynchronization therapy (CRT) settings.

14. The computing device of claim 13, wherein the processing device is configured to:

compare the calculated mechanical indices to determine which calculated mechanical index is the largest; and select the CRT settings determined to have the largest mechanical index for use during further CRT pacing.

15. A method for estimating a change in an intracardiac distance between systole and diastole, the method comprising:

generating during systole, at a pacing electrode, a first pacing pulse;

measuring, at a sensing electrode, a first electrical artifact that corresponds to the first pacing pulse;

generating during diastole, at the pacing electrode, a second pacing pulse;

measuring, at the sensing electrode, a second electrical artifact that corresponds to the second pacing pulse;

determining a first amplitude of the first electrical artifact;

determining a second amplitude of the second electrical artifact; and calculating a mechanical index based on the first amplitude and the second amplitude, wherein the mechanical index is representative of the change in the intracardiac distance.

16. The method of claim 15, wherein generating a first pacing pulse comprises generating a first pacing pulse using a pacing electrode included on a multiple-electrode lead, and wherein generating a second pacing pulse comprises generating a second pacing pulse using a sensing electrode included on the multiple-electrode lead.

17. The method of claim 15, wherein determining the first amplitude comprises subtracting a control intracardiac electrogram (IEGM) that does not include the first electrical artifact from an artifact IEGM that does include the first electrical artifact.

18. The method of claim 15, wherein calculating the mechanical index comprises calculating the mechanical index as the difference between the first amplitude and the second amplitude, divided by the second amplitude.

19. The method of claim 15, further comprising calculating a separate said mechanical index at each of a plurality of different cardiac resynchronization therapy (CRT) settings.

20. The method of claim 19, further comprising:

comparing the calculated mechanical indices to determine which calculated mechanical index is the largest; and selecting the CRT settings determined to have the largest mechanical index for use during further CRT pacing.

* * * * *